United States Patent [19]

Ackerman, Jr.

[11] 4,197,644
[45] Apr. 15, 1980

[54] ORTHODONTIC METHOD AND APPLIANCE

[76] Inventor: Richard J. Ackerman, Jr., 605 W. Dartmouth Rd., Kansas City, Mo. 64113

[21] Appl. No.: 887,119

[22] Filed: Mar. 16, 1978

[51] Int. Cl.² .............................................. A61C 7/00
[52] U.S. Cl. .................................................... 433/7
[58] Field of Search ........................................ 32/14 E

[56] References Cited

U.S. PATENT DOCUMENTS

| | | | |
|---|---|---|---|
| 3,096,584 | 7/1963 | Traiger | 32/14 E |
| 3,699,656 | 10/1972 | Scheu | 32/14 E |
| 3,738,005 | 6/1973 | Cohen et al. | 32/14 B |
| 3,827,146 | 8/1974 | Wallshein | 32/14 E |
| 3,835,538 | 9/1974 | Northcutt | 32/14 E |
| 3,835,540 | 9/1974 | Biederman | 32/14 E |
| 4,026,023 | 5/1977 | Fisher | 32/14 E |
| 4,045,871 | 9/1977 | Nelson | 32/14 E |
| 4,068,379 | 1/1978 | Miller et al. | 32/14 A |

FOREIGN PATENT DOCUMENTS

| | | | |
|---|---|---|---|
| 981973 | 6/1951 | France | 32/14 E |
| 1031602 | 6/1953 | France | 32/14 E |

OTHER PUBLICATIONS

DCA Brochure, "Fixed Maxillary Expansion Appliances".

Primary Examiner—Louis G. Mancene
Assistant Examiner—John J. Wilson
Attorney, Agent, or Firm—Thomas K. Ziegler

[57] ABSTRACT

An orthodontic method for moving maxillary teeth by spreading the midpalatal suture completely obviates the time-consuming procedure of securing the appliance to the teeth by means of orthodontic bands and brackets specially fitted around the teeth by directly bonding the appliance to lingual surface areas of the teeth. An improved maxillary expansion appliance includes a pair of U-shaped anchoring elements each having a plurality of mounting pads secured thereto which are adapted to be bonded by means of an adhesive directly to lingual surface areas of opposed maxillary teeth and form the sole points of contact between the appliance and the teeth, yet provide firm anchoring of the appliance to the teeth while significantly improving oral hygiene and eliminating the unsightly appearance of orthodontic frame work on the facial surfaces of the teeth visible when the lips are parted. The improved appliance includes shiftable structure for facilitating final fitting of the appliance to the teeth.

13 Claims, 5 Drawing Figures

ORTHODONTIC METHOD AND APPLIANCE

TECHNICAL FIELD

This invention generally relates to orthodontics, and deals more particularly with an improved orthopedic appliance and a novel method of installing the same between the opposing maxillary teeth for the purpose of moving the latter.

BACKGROUND ART

Transverse constriction of the maxillary dental arch is a condition which results in nonalignment of the posterior upper and lower teeth. One common method of expanding the maxilla to produce proper biting alignment of the affected teeth involves controlled separation of the midpalatal suture by means of an expandable, force transmitting appliance which is attached to selected sets of opposing maxillary teeth. Gradual expansion of the appliance transmits laterally outward forces on the maxilla through the teeth which, over an extended period of time, eventually separates the midpalatal suture allowing movement of the maxilla to bring the teeth into the desired alignment. In children, the midpalatal suture is essentially open and becomes fused through natural physical development after puberty, consequently, a maxillary expansion appliance is often used in connection with children to separate the suture and expand the maxilla. This orthodontic technique is employed somewhat less frequently in the case of adults having constricted palates, since the midpalatal suture fuses at approximately 18 years of age and makes separation thereof impossible without oral surgical intervention for reopening the fused suture. After the suture is opened by surgical means, however, a maxillary expansion appliance may be installed in the adult patient's palate to separate the maxilla and bring the maxillary teeth into proper biting alignment. Palatal expansion appliances are also utilized in connection with the treatment of persons having improperly developed lateral palatal shelves which result in a condition known as cleft palate. The severe maxillary constriction caused by the cleft palate condition is frequently corrected through the use of the expansion appliance in combination with surgical and prosthetic reconstruction.

The complete impact and significance of the present invention becomes evident only upon a thorough understanding and appreciation of the prior orthodontic procedure by which a maxillary expansion appliance was fitted and installed between a patient's maxillae, which will now be discussed. It is first important to recall that the object of the appliance is to move the maxillae apart themselves, rather than moving the posterior teeth with respect to the bone structure thereunder forming the maxillae. With this in mind, it is desirable to avoid any movement of the affected maxillary teeth with respect to each other during the spreading of the midpalatal suture, and in fact, the orthodontist attempts to immobilize the mentioned teeth with respect to each other so that the lateral forces generated by the appliance are fully communicated to the maxillae rather than to the teeth themselves. These functional requirements, in addition to the limited range of known orthodontic techniques for fastening appliances to the teeth, have in the past dictated the need to use traditional orthodontic bands and brackets for immobilizing the affected teeth and for attaching the appliance thereto.

Patients with constricted palates, frequently children, often have close dental crowding of the maxillary teeth which makes it virtually impossible to fit the required orthodontic bands around such teeth. Consequently, the first step in the previous technique for fitting the appliance to the patient's teeth involved the procedure of wedging the teeth apart to produce interproximal spacing between the teeth which allowed the bands to be fitted and attached therearound. Several methods may be employed to wedge the teeth apart to accomplish the necessary spacing, but all of such procedures require an extended period of time to accomplish and are extremely uncomfortable for the patient. After separating the teeth interproximally, bands were then positioned around each tooth involved. With children, it is sometimes impossible to install a band around a particular tooth due to the fact that some teeth may not protrude sufficiently beyond a gum line to present an adequate surface area to which the band may be attached. Similarly, conical or malformed teeth are difficult, and in some cases impossible to band; consequently, under these circumstances, the maxillary expansion appliance could not be employed. In other cases, the teeth may extend only a marginal distance beyond the gum line in which case the bands were installed around the exposed tooth surface areas and were then forced downwardly along the tooth into the surrounding gum; this procedure, of course, was particularly uncomfortable for the patient. In any event, after having installed the bands around the affected teeth, an impression was taken of the teeth with the bands in place, after which the impression was removed from the patient's mouth. The bands were then removed from the patient's teeth and inserted into the impression, whereupon a dental gypsum material was poured into the impression to form a model of the patient's teeth with the bands properly fastened in position therearound. With the bands fastened around the model of the teeth, a wire frame structure was then soldered to the bands in order to form a rigid assembly structurally interconnecting each of the latter, and the assembly was then attached to an expansion screw mechanism to complete the appliance. The procedure of fastening the wire structure to the bands became rather critical in order to assure that the laterally outward force produced by the expansion appliance was evenly applied to each of the teeth in a uniform manner, rather than imposing differing magnitudes of force on the teeth which might result in orthodontic movement of the latter, rather than orthopedic movement of the maxilla. After interconnecting the bands by means of the wire structure, the affected teeth were again separated interproximally by means of wedging devices or the like before the appliance and attached band assembly could be fitted onto the patient's teeth. After having separated the teeth, an adhesive dental cement was then applied to the interior surfaces of the bands. The appliance and associated band assembly was then installed as a single unit and the bands were secured, by means of the dental cement, to the teeth.

From the foregoing, it can be readily appreciated that the use of traditional, orthodontic bands for installing the expansion appliance between the patient's maxillary teeth was not only very time-consuming (and therefore costly to the patient) and painful, but was also rather imprecise and subject to human error. In fact, the prior procedure for attaching the expansion appliance to the teeth was considerably less than completely satisfactory, since the individual bands would often break loose from their associated tooth during the course of the suture opening procedure; this was primarily due to the fact that the bands could not be installed as a unit around the teeth as tightly as they might be installed on an individual basis around the teeth. Moreover, since the bands had to be installed as a single unit, the bands had to be slightly oversized to provide a fitting tolerance to assure that all the bands could be installed around their associated teeth. The prior procedure is also undesirable from the standpoint that washing out of cement around the banded teeth predisposes the latter to decalcification and later possible tooth decay. Also, it was not uncommon for one or more of the bands to become loosened from its associated tooth; under these circumstances, the entire expansion appliance and associated band assembly had to be removed from the patient's mouth, while the teeth were cleaned and again prepared for refitting of the appliance as described above.

DISCLOSURE OF THE INVENTION

The present invention provides a unique orthodontic method and structure for coupling a maxillary expansion appliance between opposing sets of maxillary teeth of a patient in order to expand the patient's constricted maxillary dental arch. The appliance includes a bidirectional, force transmitting screw assembly adapted to be installed into the patient's palate and is provided with improved structure for attaching the screw assembly between opposed maxillary teeth. In one form of the appliance, the screw assembly is mounted between a pair of molded plastic body portions which conform to the curvature of the patient's palate and each have molded therewithin the legs of U-shaped teeth anchoring wire element whose base side extends across and closely adjoins lingual surface areas of selected maxillary teeth. The wire element carries a plurality of wire mesh pads on the base side thereof which are bonded, using adhesives, to the lingual surface areas of the teeth, thereby firmly anchoring the appliance to the maxillary teeth without the need for orthodontic bands or brackets. In another form of the appliance, the legs of the wire anchoring element are elongated and are slidably received within rod bores in the screw assembly to allow rapid, initial fitting of the appliance to the patient's teeth.

BEST MODE FOR CARRYING OUT THE INVENTION

Figure 1:
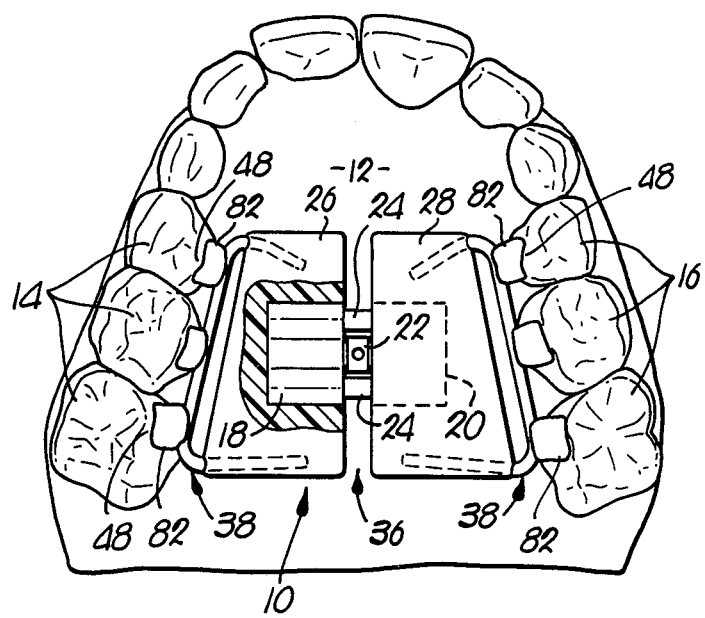
FIG. 1 is a bottom plan view of a preferred form of an appliance which forms a part of the present invention, shown installed within the palate of a patient by a novel method of attachment to the maxillary teeth of the patient, parts of the appliance being broken away in section to reveal portions of an expandable screw assembly.
Figure 2:
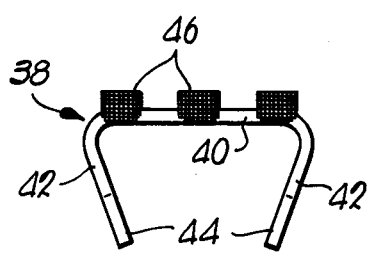
FIG. 2 is a longitudinal side view of a wire anchoring element, having been removed from the appliance.
Figure 3:
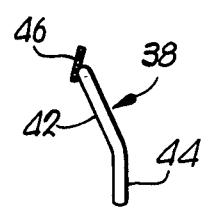
FIG. 3 is an end view of the wire anchoring element shown in FIG. 2.

Turning attention first to FIGS. 1-4, a maxillary expansion appliance, generally indicated by the numeral 10, is adapted to be entirely disposed within the palatal cavity 12 of a patient's mouth, and in force applying relationship to a selected set of the patient's maxillary teeth on opposite sides of the mouth, designated by the numerals 14 and 16 respectively. The appliance 10 includes a first and second body portion 18 and 20 respectively, each having a threaded bore therethrough. A central adjustment screw (not shown) has the opposite extremities thereof threadably received by the bores in the body portions 18 and 20, while an apertured adjustment collar 22 is secured to central stretches of the adjustment screw for purposes of allowing manual turning of the latter. Each of the body portions 18 and 20 further include a pair of additional aligned rod bores therewithin, on respective opposite sides of the above mentioned threaded bore, which slidably receive the guide rods 24.

The body portions 18 and 20 are respectively imbedded within the members 26 and 28, which members 26 and 28 may be formed as by molding any suitable nontoxic material such as metal, rubber, or plastic. Each of the members 26 and 28 includes upper surface portions 30 which generally conform to the contour of the palatal cavity 12, and in some cases, it may be desirable for the surface portions 30 to conformally contact the palate itself, while in other cases the surface portions 30 will be slightly relieved from the palatal tissue. The lower surface portions 32 of each of the members 26 and 28 are essentially coplanar and are adapted to oppose the upper surface of the patient's tongue, while the perpendicular sidewalls 34 of each of the members 26 and 28 are slightly spaced apart to form a slot 36 between the members 26 and 28 to allow access to the adjustment collar 22.

The appliance 10 further includes a generally U-shaped, anchoring element 38 having an essentially straight base side 40 and a pair of legs 42 extending toward each other and away from the base side 40 at a somewhat acute angle with respect to the latter. The anchoring element 38 may be formed from any suitable rigid stock, and may comprise a stainless steel wire having a circular cross section, one suitable type of wire being manufactured by the Rocky Mountain Orthodontics Corporation and identified by the manufacturers number E-208. The outer extremities 44 of the legs 42 are slightly angled with respect to central stretches thereof for purposes which will become later apparent. A plurality of mounting means in the nature of pad members 46 are fixedly attached along one edge of the base side 40 of the anchoring element 38, and are spaced therealong at intervals generally coinciding with the spacing between the corresponding set of maxillary teeth 14. More particularly, the pad members 46 are disposed along the edge of the base side 40 at a position and angle coinciding registration with the lingual surface areas 48 of the associated teeth 14 and 16. In the preferred form of the apparatus 10, the pad means 46 comprise stainless steel, wire mesh material such as that manufactured by T.P. Laboratories, Inc. and identified by the manufacturers number 210–216, however it is noted that any suitable nontoxic material having an irregular or pervious surface may also be suitably employed.

Figure 4:
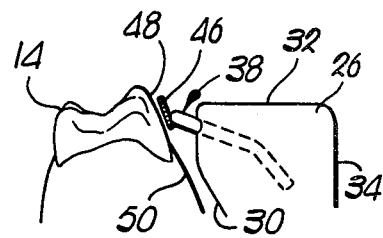
FIG. 4 is an end view of portions of the maxillary teeth and appliance shown in FIG. 1, depicting a stage in the installation of the appliance just prior to the introduction of a bonding adhesive between the teeth and the wire anchoring element.

The legs 42 of the anchoring elements 38 are imbedded in, and therefore firmly secured to, the respectively associated members 26 and 28 while the base side 40 extends laterally outward beyond the corresponding member 26 or 28 at a point adjacent the juncture of the upper surface portions 30 and the lower surface portions 32, whereby to dispose the pad members 46 immediately adjacent to, but slightly spaced from the lingual surface areas 48, as best shown in FIG. 4. It may be appreciated from viewing FIG. 4 that after a bonding adhesive has been introduced between the lingual surface areas 48 and the pad members 46, the anchoring element 38 provides the sole means for supporting and connecting the appliance between the maxillary teeth 14 and 16 in a manner that produces a spacing between the upper surface portions 30 of each of the members 26 and 28, and the palatal marginal gingiva indicated by the numeral 50.

From the foregoing description, particularly in connection with FIGS. 1 and 4, it is clear that the entire structure associated with the appliance 10 is wholly confined between the opposing lingual surface areas of the maxillary teeth 14 and 16, and does not include any structure whatsoever which contacts either the interproximal or facial areas of the teeth 14 or 16, or marginal portions of the gingiva 50. Moreover, it is apparent that the appliance 10 employs a minimum of structure, in comparison to prior art devices, for mounting the same into force applying relationship between the teeth 14 and 16.

Figure 5:
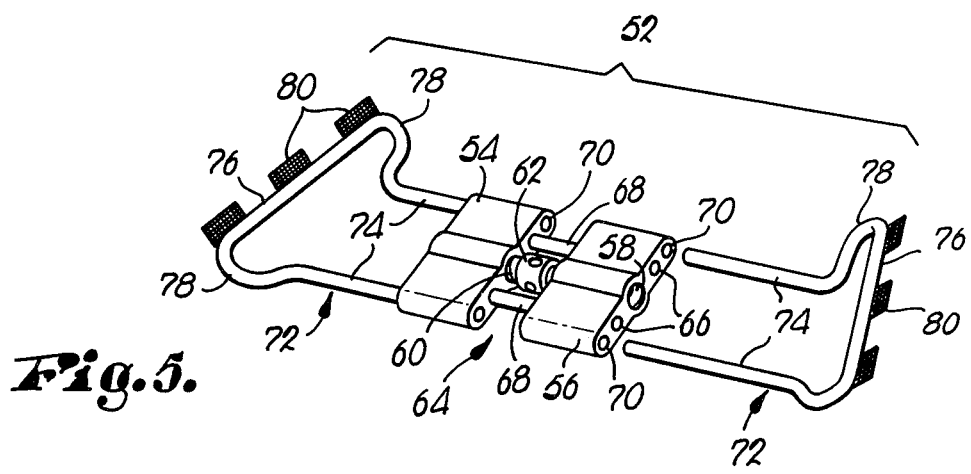
FIG. 5 is a perspective view of an alternate form of the appliance, the legs of one of the wire anchoring elements having been slightly removed from the main body of the appliance.

Attention is also now directed to FIG. 5, wherein an alternate form of the appliance 52 is depicted. The appliance 52 includes a main body consisting of a pair of body portions 54 and 56, which are each generally rectangular in shape and may be made from any suitable nontoxic material. Each of the body portions 54 and 56 include a threaded screw bore 58 transversely therethrough adjacent the longitudinal midpoint thereof. The screw bores 58 threadably receive the opposite extremities of an adjustment screw 60 having an apertured adjustment collar 62 securely fastened to central stretches thereof, within a spacing 64 between the body portions 54 and 56. The body portions 54 and 56 each include a first set of longitudinally spaced rod bores 66 transversely therethrough on respective opposite sides of the screw bore 58. A pair of guide rods 68 are respectively received within opposing ones of the rod bores 66, and each have one end thereof secured in one of the rod bores 66 associated with one of the body portions 54 or 56 while the opposite end thereof is slidable within the opposing rod bore 66 associated with the other body portion 54 or 56. A second set of rod bores 70 is provided in the opposite longitudinal extremities of the portions 54 and 56, which transversely pass through each of the latter and are disposed on opposite sides of the first set of rod bores 66. Optionally, however, the rod bores 70 need not pass entirely through the respectively associated body portions 54 and 56 into communication with the spacing 64.

Teeth anchoring elements 72 each include a pair of elongate, parallel legs 74 which are appropriately spaced apart to be received by the second set of rod bores 70 in the body portions 54 and 56 respectively. Each of the anchoring elements 72 includes a base side 76 of a length suitable to extend between the lingual surface areas of the teeth 14 and 16 to which the appliance 52 is to be attached. A looped portion 78 may be provided in each of the anchoring elements 72 between the legs 74 and base side 76 to allow the latter to be bent to an angular attitude in alignment with the lingual surface areas 48 of the teeth 14 and 16. Pad means 80, similar to the pad means 46 previously described, are secured by suitable means along the base side 76 of each of the elements 72 at spaced intervals coinciding with the spacing between the lingual surface areas 48 of the respectively associated teeth 14 and 16.

Either of the anchoring elements 38 or 72 may be constructed by first selecting a suitable length of wire in a relatively bendable state, and then bending the extremities of the wire to form the legs 42 or 74, such that the length of the base side 40 or 76 is adequate to traverse the lingual surface areas 48 of the teeth 14 or 16 to which it is to be attached. Having bent the anchoring element 38 or 72 into the appropriate shape, the pad means 46 or 80 are then attached to the base side 40 or 76 of the anchoring element 38 or 72 as by spot welding or soldering with silver solder at the appropriate intervals along the base side 40 or 76. The anchoring element 38 or 72 with the pad means 46 or 80 attached thereto is then heat tempered by any suitable means to provide the anchoring element 38 or 72 with adequate structural rigidity. In the case of the appliance 10, after tempering the anchoring element 38, the pad means 46 are then removably attached by adhesive means to the appropriate maxillary teeth 14 or 16 with the legs 42 assuming the approximate position shown in FIG. 4. Surface areas of a model (not shown) of the patient's teeth are then prepared in the normal manner using wax materials or the like, and the expansion screw device including body portions 18 and 20 are then disposed within the palatal cavity 12, after which a moldable material such as plastic is then poured into the palatal cavity 12 to form the members 26 and 28. During the preparation of the surface areas of the model, care is taken to interpose a mold material such as wax between the marginal gingiva and upper surface portions 30 of the members 26 and 28 to assure that a sluiceway is provided therebetween adjacent the base side 40 of the anchoring element 38 for reasons which will become later apparent. After molding the members 26 and 28, the assembled appliance 10 may be removed from the model and appropriately cleaned and conditioned in preparation for installation of the appliance 10 into the patient's palate.

The first steps in installing the appliance 10 into the patient's palatal cavity 12 consist of isolating the maxillary teeth 14 and 16 for access thereto, drying each of the same and then etching, by conventional procedures, portions of the lingual surface areas 48 of the maxillary teeth 14 and 16 to which the appliance 10 will be attached. A suitable bonding adhesive indicated by the numeral 82 in FIG. 1 is then applied to each of the pad means 46 associated with both sets of maxillary teeth 14 and 16 respectively. One adhesive suitable for use is manufactured by the L. D. Caulk Company and is identified by the manufacturer's trade name of Auto-Tach, however several other known removable adhesive materials may also be effectively employed. After applying the adhesive material to each of the pad means 46, the appliance 10 may be inserted into the patient's palatal cavity 12, in a manner to simultaneously bring each of the pad means 46 into close proximity to the associated lingual surface areas 48 of the teeth such that the adhesive material contacts each of the latter. The appliance 10 is then held in position by the manual application of gentle pressure until the bonding material cures sufficiently to hold the appliance in place between the maxillary teeth 14 and 16. After the bonding material has completely cured, a wrench means (not shown) may be inserted into the adjustment collar 22 to allow turning of the latter resulting in lateral expansion of the body portions 18 and 20, which communicates laterally outward forces through the members 26 and legs 42 of the anchoring element 38, which inturn imposes a transversely outward force on each of the maxillary teeth 14 and 16 applied through the pad means 46 and bonding adhesive 82 between the lingual surface areas 48 and the base side 40 of each of the anchoring elements 38. Routine clinical procedure may then be followed consisting of selectively manipulating the adjustment collar 22 over a period of time to gradually expand the appliance 10 in order to separate the midpalatal suture and thereby move the maxillary teeth 14 and 16 transversely outward. In order to remove the appliance 10 from the maxillary teeth 14 and 16, the legs 42 of the anchoring elements 38 are severed from the base side 40 of the latter, thereby allowing the main central portion of the appliance 10 consisting of the members 26 and 28 to be removed from the palatal cavity 12. Each bond 82 is then mechanically broken away from its respectively associated tooth using conventional orthodontic instruments, after which the tooth is polished. During the course of the suture opening treatment, in the event that one or more of the bonds between the anchoring elements 38 and the teeth 14 or 16 is fractured or breaks loose, the defective bond and the associated tooth or teeth may be cleansed and conditioned as previously described and rebonded to the corresponding anchoring element 38 without the need for removing the appliance 10 from the patient's mouth, which would otherwise necessitate removing the remaining good bonds and subsequently rebonding the entire appliance 10 in the manner described above.

The novel construction of the alternate form of the appliance 52 substantially simplifies the above discussed procedure for fitting and installing the appliance into force coupling relationship between the teeth 14 and 16 within the palatal cavity 12. The legs 74 of each of the anchoring elements 72 are first inserted into the corresponding rod bores 70, and the entire appliance 52 may then be disposed within the palatal cavity of a model of the patient's teeth, or alternatively, the appliance 52 may be inserted directly into the patient's palatal cavity 12. In those cases where it is desired to first fit the appliance 52 to a model of the patient's teeth, the base sides 76 are manipulated by bending the anchoring element 72 at the looped portion 78 thereof until the pad means 80 are disposed adjacent each of the lingual surface areas 48 of the associated maxillary teeth 14 or 16. In some cases, it may be necessary to bond the pad means 80 to the lingual surface areas 48 of the model of the teeth 14 or 16 during this mentioned procedure, but in any event, after the base sides 76 of the anchoring elements 72 have been bent to their proper attitudes, and the legs 74 are properly positioned within the rod bores 70, the legs 74 may be then secured to the corresponding body portions 54 and 56, by any suitable means, such as welding, soldering or crimping. After fitting the appliance 52 to the model of the patient's teeth, the appliance may be installed within the palatal cavity 12 and attached to the teeth 14 and 16 in a manner essentially identical to that described with reference to the installation of the appliance 10.

Alternatively, the appliance 52 may be installed, in many cases, directly into the patient's palatal cavity 12 without the need for prefitting the appliance to a model of the patient's teeth. Under these circumstances, after having inserted the legs 74 of the anchoring elements 72 into the rod bores 70, the appliance 52 is disposed within the patient's palatal cavity 12 and the legs 74 are slidably moved laterally outward from the corresponding body portion 54 and 56 until the pad means 80 contact or are in close proximity with the lingual surface areas of the respectively associated teeth 14 and 16. The amount of extension of the legs 74 from the corresponding body portions 54 and 56 is then recorded by placing an indicating mark, using any suitable marking means, on the legs 74 immediately adjacent the openings in the lateral sides of the body portions 54 and 56 formed by the second set of rod bores 70. The legs 74 are then retracted slightly into the body portions 54 and 56 and the appliance 52 is removed from the patient's mouth. With the aid of the indicating marks, the legs 74 are then extended once again to the precise position in which they were extended within the patient's mouth, and the legs 74 are secured to the body portions 54 and 56 as discussed previously. With the legs thus secured in place, the appliance 52 is reinserted into the patient's palatal cavity 12 and the pad means 80 are bonded to the respectively associated teeth 14 or 16 in the manner previously indicated.

From the foregoing description of the construction and method of installation of the appliances 10 or 52, it is clearly apparent that both of the appliances 10 and 52 are entirely disposed within the portion of the palatal cavity 12 between lingual surfaced areas of the opposing sets of maxillary teeth 14 and 16, and present no structure whatsoever on the facial areas of such teeth which is exposed to view upon parting of the patient's lips. In addition to the obvious fact that each of the appliances 10 or 52 may be fitted to a model of the patient's teeth and then installed in the patient's palatal cavity in a relatively short time compared to prior art designs employing bands and brackets, the appliances 10 and 52 significantly improve oral hygiene compared with prior art appliances inasmuch as a sluiceway is provided between the appliance 10 or 52, the teeth 14 or 16, and underlying marginal gingiva 50. Moreover, oral hygiene is also improved with the appliance 10 or 52 inasmuch as the interproximal areas between the teeth 14 or 16 may be simply cleansed using dental floss, whereas prior art appliance designs employing bands or braces, naturally prevented dental flossing. It is further important to observe that the actual contact area defined by the bonded zone between the pad means 46 or 80 and the lingual surface areas 48 of the teeth 14 and 16 is relatively small, particularly in comparison to the surface areas affected by prior art methods of attaching an expansion appliance to the teeth. Consequently, the appliances 10 or 52 may be effectively employed with those persons having maxillary teeth which present a minimal surface area above the marginal gingiva.

Clinical testing of the invention has yielded particularly satisfactory, and in fact, somewhat unexpected results. Heretofore, it was believed that orthodontic bands and brackets were required to assure that the maxillary teeth were immobilized while force was applied thereto by the appliance during the opening of the suture, and considerable orthodontic structure was often employed to accomplish this objective. In spite of the prior art teachings, however, the use of a single wire member such as the anchoring elements 38 or 72 having a stretch thereof bonded to the lingual surface portions of the maxillary teeth has been found to be completely satisfactory for immobilizing the maxillary teeth and transmitting the applied force to the opposing maxillae. In fact, it is believed that the present invention may even yield results superior to those achieved with prior art type appliances, since the loose fitting nature of some bands in the prior art appliances often allowed some interproximal relative movement of the maxillary teeth to which it was attached.

INDUSTRIAL APPLICABILITY

The construction and method of installing the appliance having improved attachment structure has been made amply clear by the foregoing description. It is apparent that the teeth anchoring elements 38 or 72 may comprise any of various geometrical configurations which present appropriate mounting structure connecting the lingual surface areas 48 and the appliance 10 or 52. It is also to be noted that any of various bonding techniques for connecting portions of the anchoring elements 38 or 72 with the lingual surface areas 48 of the teeth may be employed including biochemical joining processes such as protein attachment. Finally, although pad means 46 and 80 have been described as consisting of discrete, separate mesh-like members, it is recognized that suitable pad means may be provided integral with the wire or other material forming the base sides 40 and 76 by stamping or molding portions of the base sides 40 or 76 to produce a bondable surface area permitting adequate adhesion between the anchoring element 38 or 72 and the teeth 14 or 16.

From the foregoing, it is clear that the invention provides a novelly constructed maxillary expansion appliance and method for attaching the same between lingual surface areas of the maxillary teeth which is particularly economical and effective in use. It is recognized, of course, that those skilled in the art may make various modifications or additions to the embodiments chosen to illustrate the invention without departing from the gist and essence of the present contribution to the art. Accordingly, it is to be understood that the protection sought and to be afforded hereby should be deemed to extend to the subject matter claimed and all equivalents thereof fairly within the scope of the invention.

Having thus described the invention, what is claimed as new and desired to be secured by Letters Patent is:

1. A method of coupling a maxillary expansion appliance disposed within the palatal cavity of a patient into force applying relationship to opposing selected sets of maxillary teeth of the patient, without the employment of orthodontic bands upon said teeth, including the steps of:
    (A) positioning an anchoring element of said appliance adjacent lingual surface areas of each of said teeth in said selected sets thereof; and
    (B) then, bonding portions of said element directly to said lingual surface areas of said teeth to form the sole points of contact between said appliance and said teeth in said selected sets thereof.

2. The invention of claim 1 wherein step (A) is performed by aligning said portions of said anchoring element in registration with said lingual surface areas of the respectively associated teeth in said selected set of the latter.

3. The invention of claim 1, wherein step (B) is performed by introducing an adhesive material between said portions of said anchoring element and said lingual surface areas of said teeth in said selected sets of the latter.

4. The invention of claim 3, further including prior to performing step (B), the step of:
    (C) conditioning said lingual surface areas of said teeth in said selected sets of the latter whereby to increase the adhesion between said adhesive and said latter mentioned teeth.

5. The invention of claim 4, wherein step (C) is performed by etching said lingual surface areas.

6. The invention of claim 3, further including, after performing step (B) by introducing said adhesive material, the step of:
    (C) applying a compressive force between said portions of said anchoring element and said lingual surface areas whereby to urge the former toward the latter until said adhesive material firmly bonds said anchoring element portions to said lingual surface areas of said teeth in said selected sets of the latter.

7. An orthodontic appliance for spreading the midpalatal suture of a patient and adapted to be attached to the patient's maxillary teeth without the need for orthodontic bands, including:
    a main body comprising first and second body portions;
    structure shiftably coupling said body portions, including manually operable force transmitting mechanism for urging said body portions to shift away from each other;
    a pair of generally U-shaped rigid anchoring elements respectively mounted on said body portions and extending beyond the latter,
    each of said anchoring elements comprising a generally straight base side and a pair of legs extending away from said base side,
    said base sides of said anchoring elements including portions adapted to extend in a direction along, and adjacent to, lingual surface areas of respectively associated selected sets of opposing maxillary teeth when said appliance is installed in the patient's palatal cavity; and
    means carried by each of said anchoring elements adjacent said base side portions thereof for mounting said anchoring elements only on said lingual surface areas of said teeth,
    said mounting means including a plurality of pad means on said base side of each of said anchoring elements and defining bondable surface portions, said bondable surface portions generally conforming to the respectively associated lingual surface areas of said teeth and adapted to adhere to an adhesive material introduced between said pad means and said lingual surface areas of said teeth,
    the entire appliance being entirely disposable between said lingual surfaces of said opposing maxillary teeth in said set of the latter.

8. The invention of claim 7, wherein each of said plurality of pad means comprise a mesh-like material which is pervious to said adhesive material.

9. The invention of claim 8, wherein: said anchoring elements each comprise a stainless steel wire, and said pad means comprises a stainless steel material, said pad members means being secured to portions of said base side of each of said anchoring elements by a weld.

10. The invention of claim 8, wherein:

each of said body portions includes a molded plastic member including surface areas conforming to portions of the surface areas of the patient's said palate, and said legs of said anchoring elements are secured in respectively associated ones of said plastic members.

11. The invention of claim 10, wherein the ends of each of said legs of said anchoring elements form an angle with respect to intermediate stretches thereof.

12. The invention of claim 7, wherein:

said body portions each include a first pair of spaced rod bores each generally aligned with the direction of shifting of said body portions, and said coupling structure comprises a pair of rod members having the opposite extremities thereof slideably received within said first pair of rod bores respectively associated with said body portions, said rods and said first pair of rod bores cooperatively functioning with each other to slideably guide said body portions for movement toward and away from each other, said body portions each including a second pair of spaced rod bores therein laterally spaced from said first part thereof for respectively receiving said legs of one of said anchoring elements therewithin, said legs being slidable within said second pair of rod bores toward and away from said lingual surface areas of said teeth to allow initial fitting of said appliance to said patient prior to actual mounting of said appliance to said lingual surface areas of said teeth.

13. The invention of claim 12, wherein each of said second pair of rod bores extend completely through the respectively associated body portion.

* * * * *